United States Patent [19]
Raley

[11] Patent Number: 6,014,576
[45] Date of Patent: Jan. 11, 2000

[54] SEGMENTED PHOTOPLETHYSMOGRAPHIC SENSOR WITH UNIVERSAL PROBE-END

[75] Inventor: Dena M. Raley, Louisville, Colo.

[73] Assignee: Datex-Ohmeda, Inc., Louisville, Colo.

[21] Appl. No.: 09/031,575

[22] Filed: Feb. 27, 1998

[51] Int. Cl.[7] ....................................... A61B 5/00
[52] U.S. Cl. ........................ 600/344; 600/310; 600/322
[58] Field of Search .................................. 600/310, 322, 600/323, 326, 333, 344

[56] References Cited

U.S. PATENT DOCUMENTS

5,058,588  10/1991  Kaestle ...................................... 600/323
5,249,576  10/1993  Goldberger et al. ..................... 600/323

*Primary Examiner*—Eric F. Winakur
*Attorney, Agent, or Firm*—Holme Robert & Owen LLP

[57] ABSTRACT

A two piece probe having a universal probe end and an interconnect cable segment provides for the use of the universal probe end with a variety of different photoplethysmographic devices. The universal probe end includes a detector, a substrate for removably affixing the probe end to a patient, a window or aperture and a connector. The interconnect cable has a connector mated to the connector on the probe end for mechanical and electrical connection of the probe-end to the interconnect cable and the photoplethysmographic monitor. The connector end of the interconnect cable also houses a plurality of emitters which are directed through the window or aperture in the probe end in order to illuminate the patient. The interconnect cable also houses the resistors or other elements which identify the type of probe, monitor manufacturer or actual emitter wavelengths. Alternatively, the emitters may be housed in the main monitor and an optical fiber may be used to direct light to the patient. An electrical conductor transmits light received by the detector back to the photoplethysmographic monitor.

21 Claims, 7 Drawing Sheets

SEGMENTED PHOTOPLETHYSMOGRAPHIC SENSOR WITH UNIVERSAL PROBE-END

FIELD OF THE INVENTION

This invention related to medical monitoring probes used in photoplethysmographic monitors and, in particular, to a probe architecture that enables the user of a photoplethysmographic monitor to use a universal probe-end for all monitors in combination with a probe-interconnect cable which is designed for a specific type of monitor.

BACKGROUND OF THE INVENTION

It is a problem in the field of medical monitoring instruments to manufacture a photoplethysmographic probe that satisfies a number of diverse and sometimes contradictory requirements. It is important that the probe both be simple to use and conform to a variety of patients who differ in size and shape. The probe must be securely affixable to the patient, such as on a patient's appendage, without requiring complex structures or elements that can irritate the patient. In addition, in order to reduce the risk of infection and contamination, at least a portion of the probe should be built to be disposable so that the probe is used one or more times with the patient and can then be destroyed. The disposable portion of the probe must be inexpensive so that it can be disposable after use and yet the patient must be shielded from any potentially dangerous electrical signals or heat produced by the probe. The probe must also reliably and accurately perform the required blood analyte measurements. The probe, cable and monitoring instrument are all subjected to a hostile environment and must be manufactured to be rugged to survive rough handling and the presence of highly reactive fluids.

Another problem with present photoplethysmographic probes is the proliferation of probe types and monitor models. The number of manufacturer designs probes for use with their specific monitors. Also, the types of photoplethysmographic monitors continues to increase. One of the primary uses of photoplethysmography has been the monitoring of the oxygen saturation of a patient's blood. However, there is a desire to expand the use of photoplethysmography into the monitoring of additional blood analytes such as carboxyhemoglobin, methemoglobin and other dyshemoglobins. This proliferation of monitor types will add additional confusion in the health care environment due to the number of additional probe types which will be offered with these new monitors.

In the specific field of pulse oximetry, the light beams are typically generated by a probe using light emitting diodes (LEDs) that produce light beams at red and infrared wavelengths. Various manufacturers use different wavelengths of LED's in illuminating the tissue of a patient. Additionally, many manufacturers use LED's which produce light having a spectral content characterized by a center wavelength which varies from the nominal wavelength of the LED. Therefore, many photoplethysmographic probes use one or more means for identifying characteristics about the probe being used. One common identification means is a resistor which resides in the probe and identifies the spectral characteristics of the emitters being used in the probe thereby enabling the photoplethysmographic monitor to utilize the correct calibration data when generating the blood analyte level. Another use of the identification means is identifying the type or manufacturer of a probe. Presently, however, there are no probes which can universally be used with all manufacturer's phtotoplethysmograhpic monitors.

In future photoplethysmographic systems it may be preferable to use laser diodes, which produce a beam of substantially monochromatic light at or exceeding the light power available from light emitting diodes that are typically used in photoplethysmography. The difficulty with laser diodes is that their cost currently prevents them from being used in a disposable probe. Placement of the laser diode in the monitoring instrument necessitates the use of one or more fiber optic strands in the cable that interconnects the disposable probe with the monitoring instrument. The cable in a hospital environment typically suffers rough handling and the life of the fiber optic strands in the connector cable can be fairly limited, thereby increasing the effective cost of the disposable probe since the cable must typically be replaced on a fairly frequent basis.

Alternatively, the laser diodes can be placed in a segment of the interconnect cable between the monitor and the patient end of the probe. This, however, still requires that the segment of the interconnect cable housing the laser diodes be reusable in order to reduce costs.

SUMMARY OF THE INVENTION

The above-described problems are solved and a technical advance achieved in the field of medical monitoring instruments by the apparatus of the present invention which makes use of a universal probe-end that can be attached to a plurality of monitor specific interconnect cables. This enables the health care provider to stock only one type of disposable probe-end. The reusable manufacturer specific interconnect cable can remain attached to the monitor with which it is being used until the reusable cable requires replacement. In the preferred embodiment disclosed herein, the disposable probe-end has a u-shaped channel for receipt of a u-shaped interconnect cable end portion which houses either the required LED's, laser diodes or optical fiber and mirrors for illuminating the tissue of a patient. The disposable probe-end may include a window in order to protect the patient from excess heat being emitted form the light sources and to protect the reusable interconnect cable from contamination. The required identification means is housed in the reusable interconnect cable, thus, the disposable probe-end can have truly universal application across all photoplethysmographic monitors.

DETAILED DESCRIPTION

The apparatus of the present invention represents a photoplethysmographic probe architecture which will reduce the proliferation of disposable probe types and result in cost-savings and ease of use for the health care provider.

One type of photoplethysmographic monitor, a pulse oximeter, is frequently used to monitor the condition of a patient in a hospital setting. The pulse oximeter instrument noninvasively measures the oxygen saturation of the arterial blood and produces a human readable display that indicates both the patient's heart rate and the oxygen saturation of the arterial blood. These readings are important to enable the medical staff to determine whether the patient's respiratory system is functioning properly, supplying sufficient oxygen to the blood.

A pulse oximeter instrument operates by use of a probe that illuminates an appendage of the patient (such as a finger, earlobe, toe, neonatal appendages, or the nasal septum) that is rich in arterial blood and measures the differential absorption of the light by the pulsatile portion of the arterial blood flow to thereby determine oxygen saturation of the arterial blood. The pulse oximeter instrument makes use of a plurality of light-emitting devices, each of which transmits light at a predetermined wavelength, which wavelengths are selected such that at least one is highly absorbed by oxygenated hemoglobin in the arterial blood and at least one is highly absorbed by reduced hemoglobin in the arterial blood. The amount of absorption of the light beams generated by these light emitting devices that are located in the probe is a measure of the relative concentration of the various hemoglobin species contained in the arterial blood. The absorption of the light that illuminates the appendage of the patient includes a constant portion that is a result of skin, bone, steady-state (venous) blood flow and light loss due to various other factors. The pulsatile component of absorption is due to the pulsatile arterial blood flow and is a small fraction of the received signal and is used by the pulse oximeter instrument to perform its measurements. It is also possible to measure additional analytes in the arterial blood, such as additional dyshemoglobins, with one additional wavelength of light for each component.

The measurements are computed by sampling the output of the light detector located in the probe to determine the incremental change in absorption of the various wavelengths of light that are used to illuminate the appendage of the patient. These incremental changes in light absorption are then used to compute the oxygen saturation of the arterial blood as well as the patient's pulse rate. Since the pulsatile component of the signals received by the light detector represent only a small fraction of the incident light, it is important that the incident light be of significant magnitude to result in transmitted signals that have sufficient amplitude to provide accurate readings. In addition, the probe containing the light-emitting devices and the light detector must be placed in intimate contact with the skin of the patient to obtain the most accurate readings.

Figure 5:
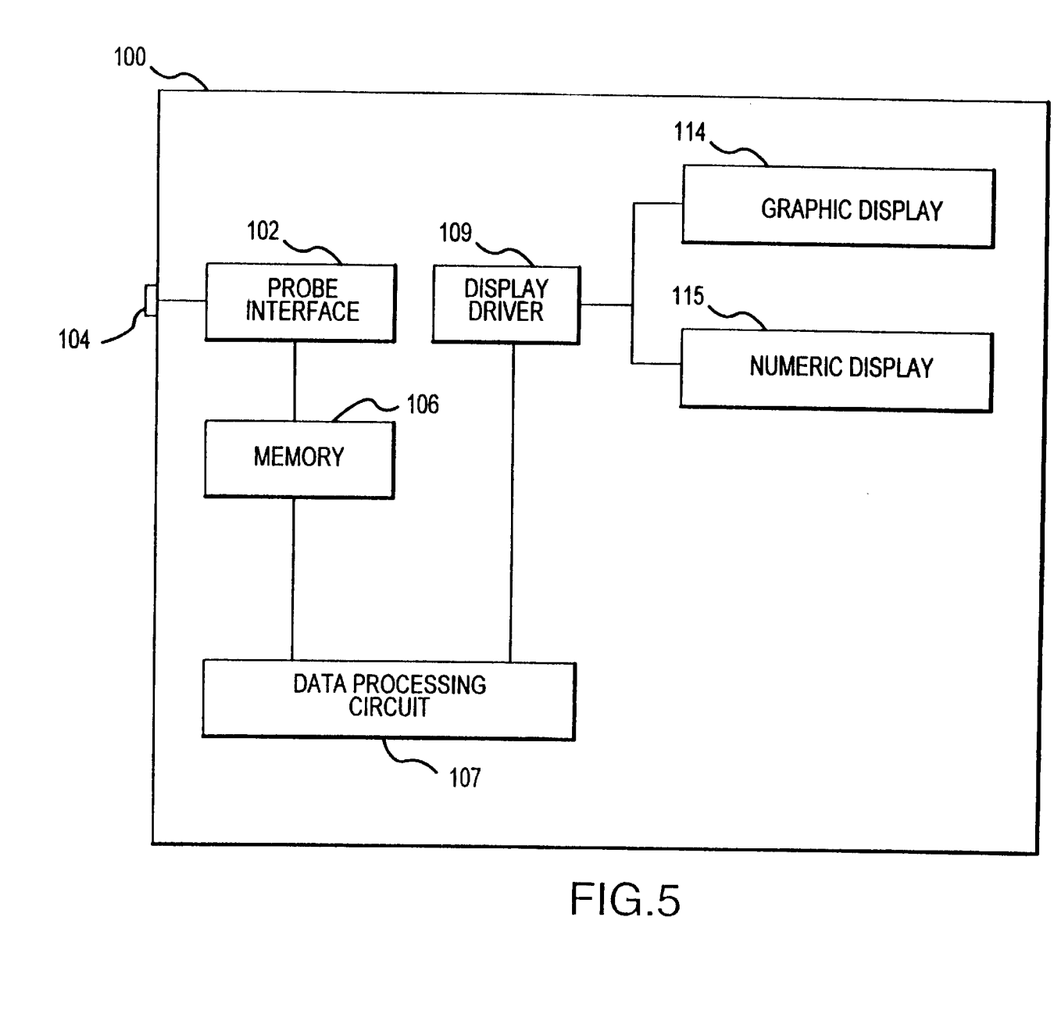
FIGS. 5 and 6 illustrate the two types of photoplethysmographic monitors.
Figure 6:
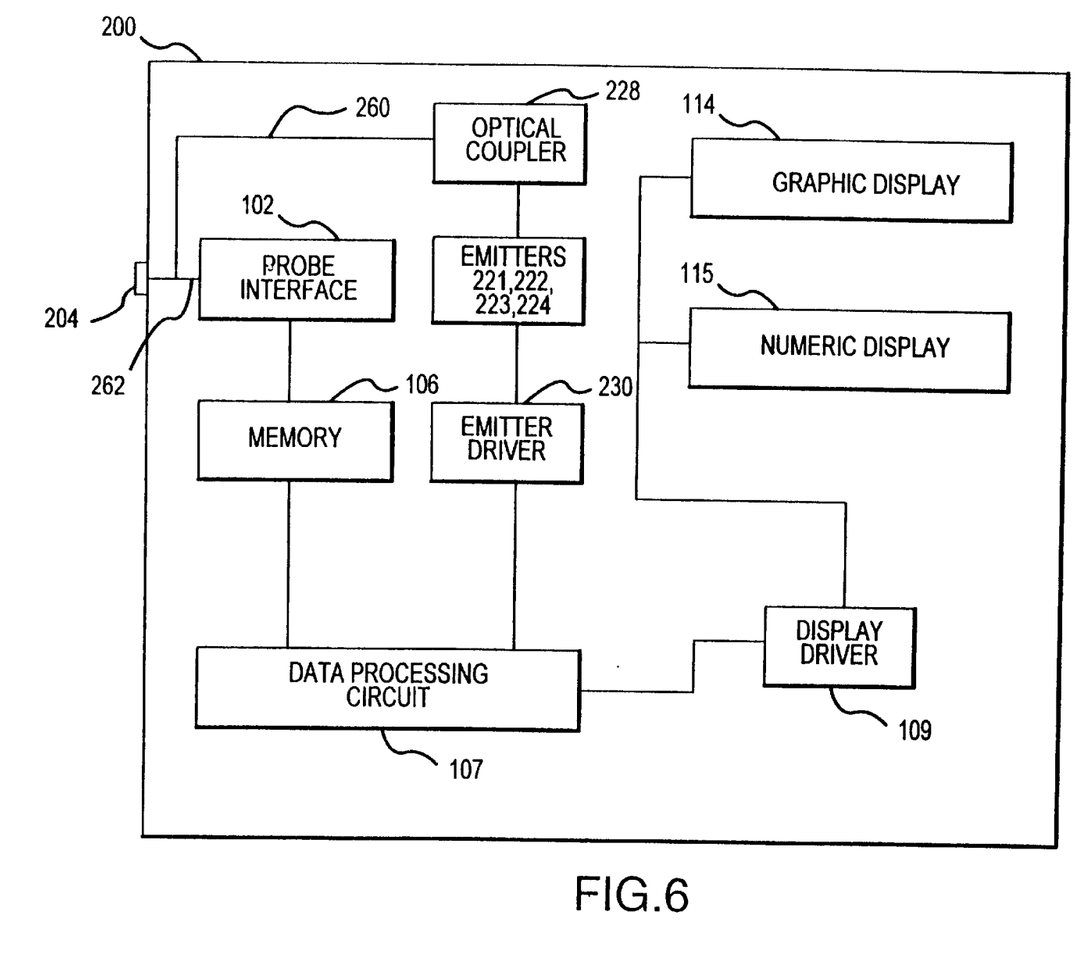

Referring to FIGS. 1, 2, 3, 4, 5 and 6, the probe 40 of the present invention is designed for use with one of two basic photoplethysmographic monitor architectures depicted in FIGS. 5 and 6. FIG. 5 depicts one of the monitor architectures in which the monitor 100 communicates with probe 40 through socket 104 and mating interconnect cable plug 42. The configuration of plug 42 depends on the type and manufacturer of monitor 100. For example, if the monitor 100 is capable of measuring a plurality of blood analyte concentrations such as O2Hb, RHb, COHb and MetHB then plug 42 and interconnect 104 will contain sufficient electrical connectors 46 to interconnect probe interface 102 with a plurality of emitters 21, 22, 23 and 24 located in the connector-end 25 of interconnect cable segment 20. In a preferred embodiment, the plurality of emitters 21, 22, 23 and 24 each emit light having a distinct spectral content characterized by a distinct center wavelength denoted by $\lambda_1$ $\lambda_2$ $\lambda_3$ and $\lambda_4$. These emitters may be light-emitting-diodes (LED's) or laser diodes. It is also possible to filter a broadband light source to produce light having four spectral peaks of differing wavelengths. In a photoplethysmographic instrument designed to generate four blood analyte levels, the preferred embodiment is to use at least four separate emitters each producing light with a distinct spectral content. If fewer blood analyte levels are desired then fewer emitters may be used either in the interconnect cable. For example, in a probe made according to the present invention for use with a standard pulse oximeter, only two emitters would be needed in the interconnect cable.

Probe identifier 47 is located in cable 28, for example in plug 42, and provides a means for identifying the type or family of the probe (ear, finger, toe etc.) or a means for identifying the manufacturer of the probe or a means for identifying the actual center wavelength of each of the plurality of emitters in the interconnect cable. The configuration of plug 42 and probe identifier 47 will be dictated by the photoplethysmographic monitor for which interconnect cable 28 is designed. Probe identifier 47 may be a resistor or set of resistors, a diode or set of diodes or some other electrical identifier. It is also possible that more than one identier may be necessary if, for example, information regarding both probe family as well as actual emitter wavelength must be communicated from the interconnect cable to the photoplethysmographic monitor.

The intensity of light transmitted through the tissue under test is measured by one or more photodetectors 13 which are located in the disposable probe-end 10. Photodetector 13 provides a signal corresponding to the intensity of light received denoted $I_{\lambda 1}$, $I_{\lambda 2}$, $I_{\lambda 3}$ and $I_{\lambda 4}$. This signal is then electrically routed back to the monitor 100 through cable 28, plug 42 and socket 104 to the probe interface 102. In the monitor the analog received intensity signals, $I_{\lambda 1}$, $I_{\lambda 2}$, $I_{\lambda 3}$ and $I_{\lambda 4}$ are converted into digital signals through a well-known analog to digital (A/D) converter. The intensity signals are then stored in memory 106 and manipulated in data processing circuit 107 of the monitor 100 according to data processing instructions stored in memory 106 and executed by the data processing circuit 107 in order to determine an estimate of the blood analyte levels output as a percentage concentration. Blood analyte levels (output as percentages) may then be displayed via display driver 109 and graphic display 114 and/or numeric display 115.

Figure 3:
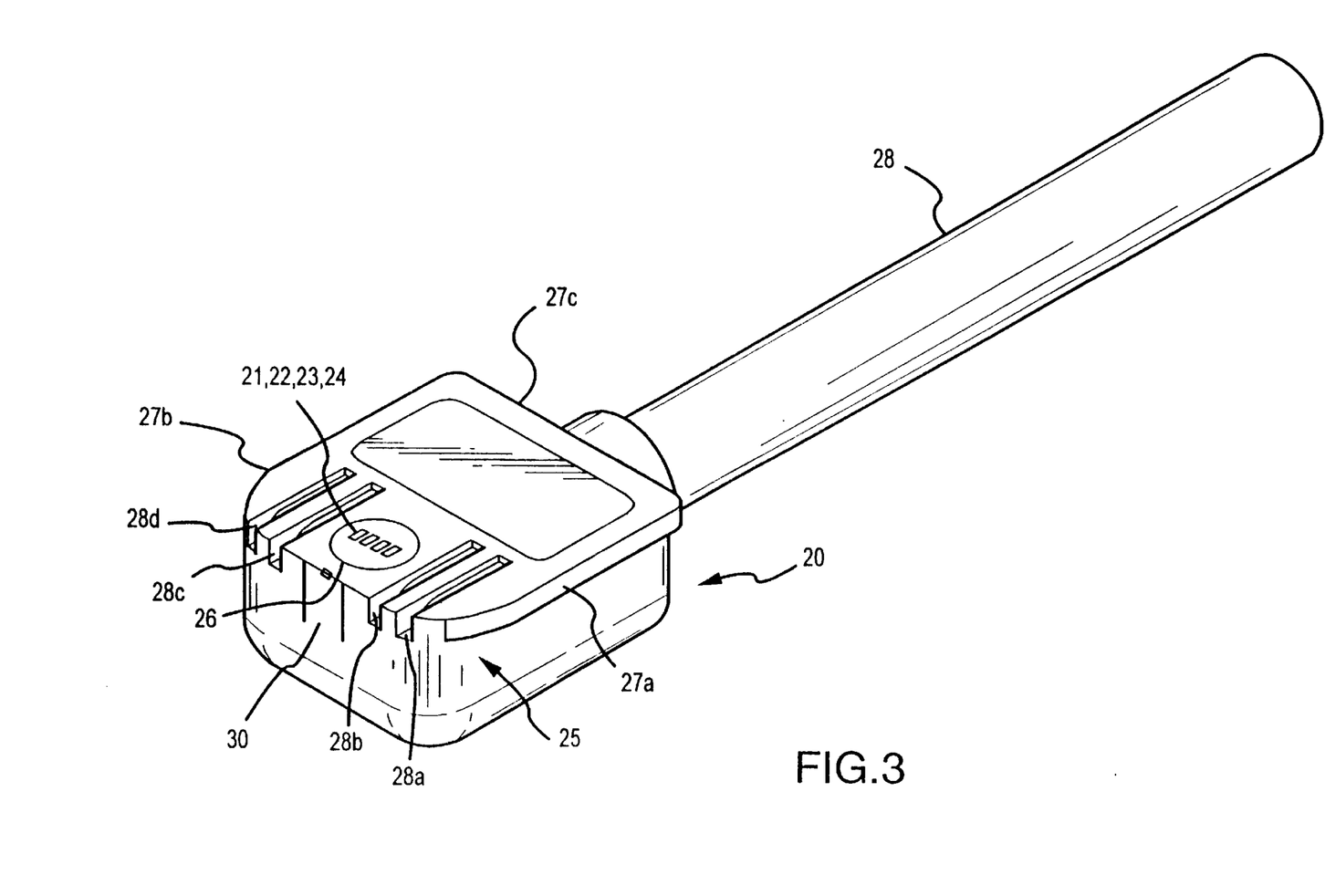
FIG. 3 is a bottom perspective view of the interconnect cable segment of one embodiment of the present invention.
Figure 3B:
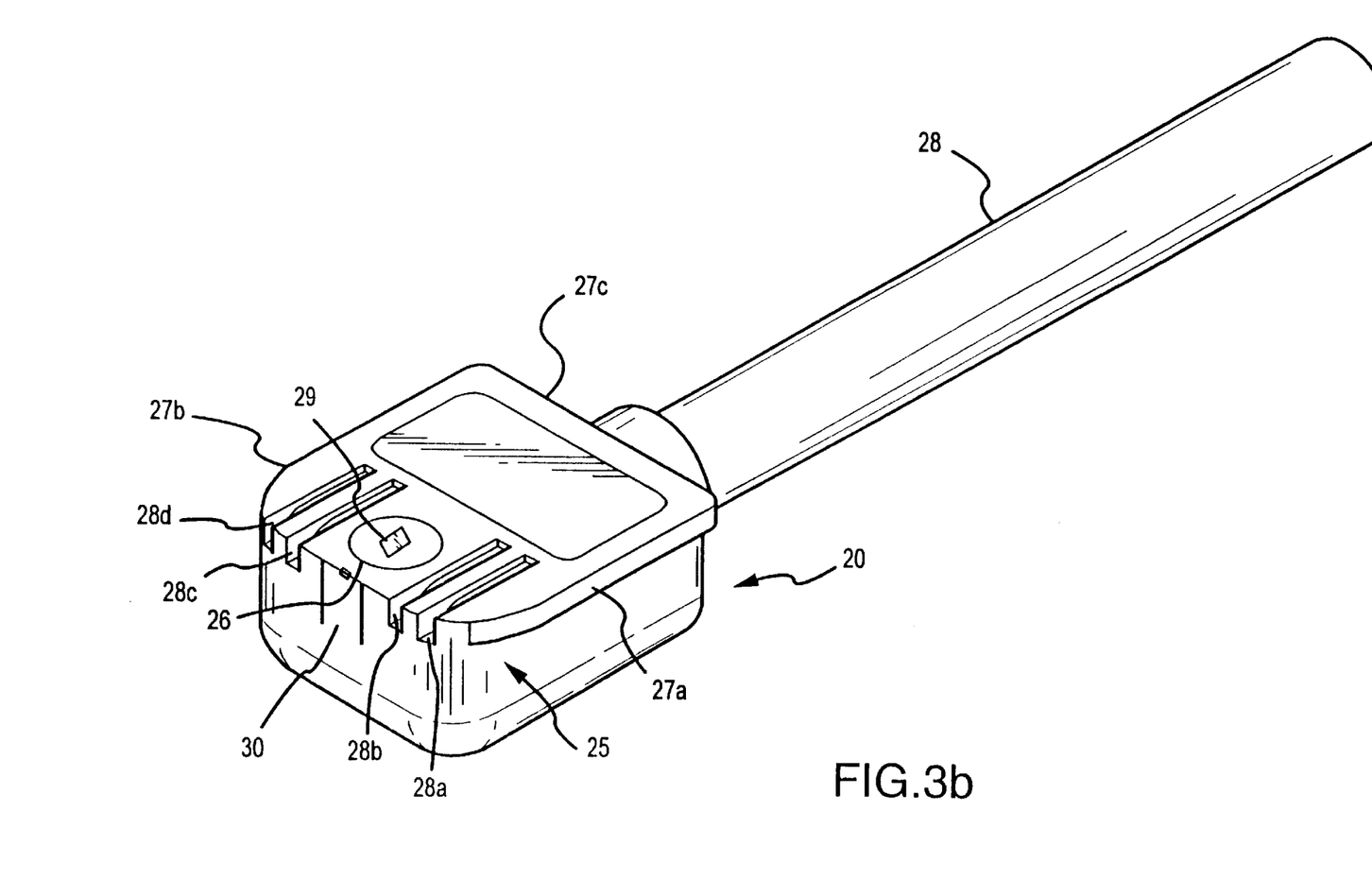
FIG. 3b is a bottom perspective view of the interconnect cable segment of an alternative embodiment of the present invention.
Figure 4:
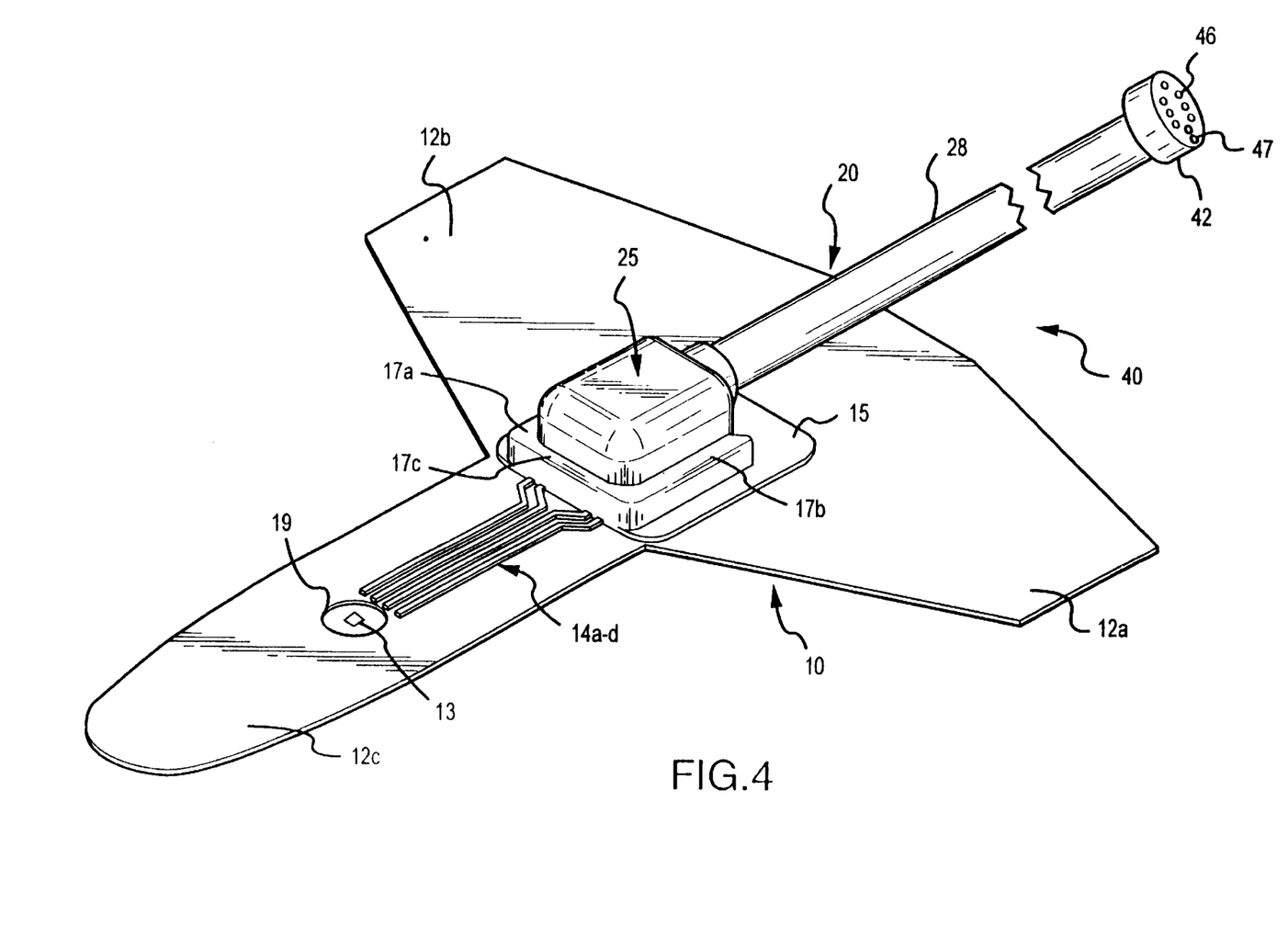
FIG. 4 is a top perspective view of the combined probe-end and interconnect cable segment of an embodiment of the present invention.

An alternative method of implementing a photoplethysmographic monitor is depicted in FIG. 6 and operates in conjunction with the alternative probe embodiment in FIG. 3b. The emitters 21, 22, 23 and 24 (which may be LED's or laser diodes, but which are preferably laser diodes) are housed in the monitor 200. The emitters 21, 22, 23 and 24 are driven by emitter driver 230 which is controlled by the data processing circuit 107. The emitted light is then combined by an optical coupler 228 and transmitted to the probe 40 by internal optical fiber 260 which is coupled to an optical fiber or other such optically transmissive material (not shown) internal to interconnect cable segment 28. Thus, plug 42 and connector 204 now includes electrical conductors for connecting photodiode 13 back to the probe interface 102 and an optical connector for connecting optical fiber 260 to an optical fiber (not shown) located in cable 28. The light transmitted through the optical fiber 260 and transmitted through the optical fiber located in cable 28, reflects off mirror 29 of FIG. 3b in connector end 25 and passes through window or opening 26 and window 16 in probe-end 10 and impinges on the tissue of the patient.

Transmitted light is received by photodetector 13 which send an electrical signal back to the probe interface 102 through the electrical conductors in cable 28 and electrical pathway 262 in monitor 200. The probe interface 102 converts the analog signal to a digital signal and transmits the signal to memory 106 and on to data processing circuit 107 for processing and display of blood analyte concentration values using graphic display 114 and numeric display 115 driven by display driver 109. The transmission of the emitted light can be controlled in a time division multiplexing manner and an optical coupler 228 can be used to provide a means for combining multiple emitters onto one strand of optical fiber 260. Alternatively, the plurality of emitters may be placed or abutted against optical fiber 260.

The Probe

Figure 1:
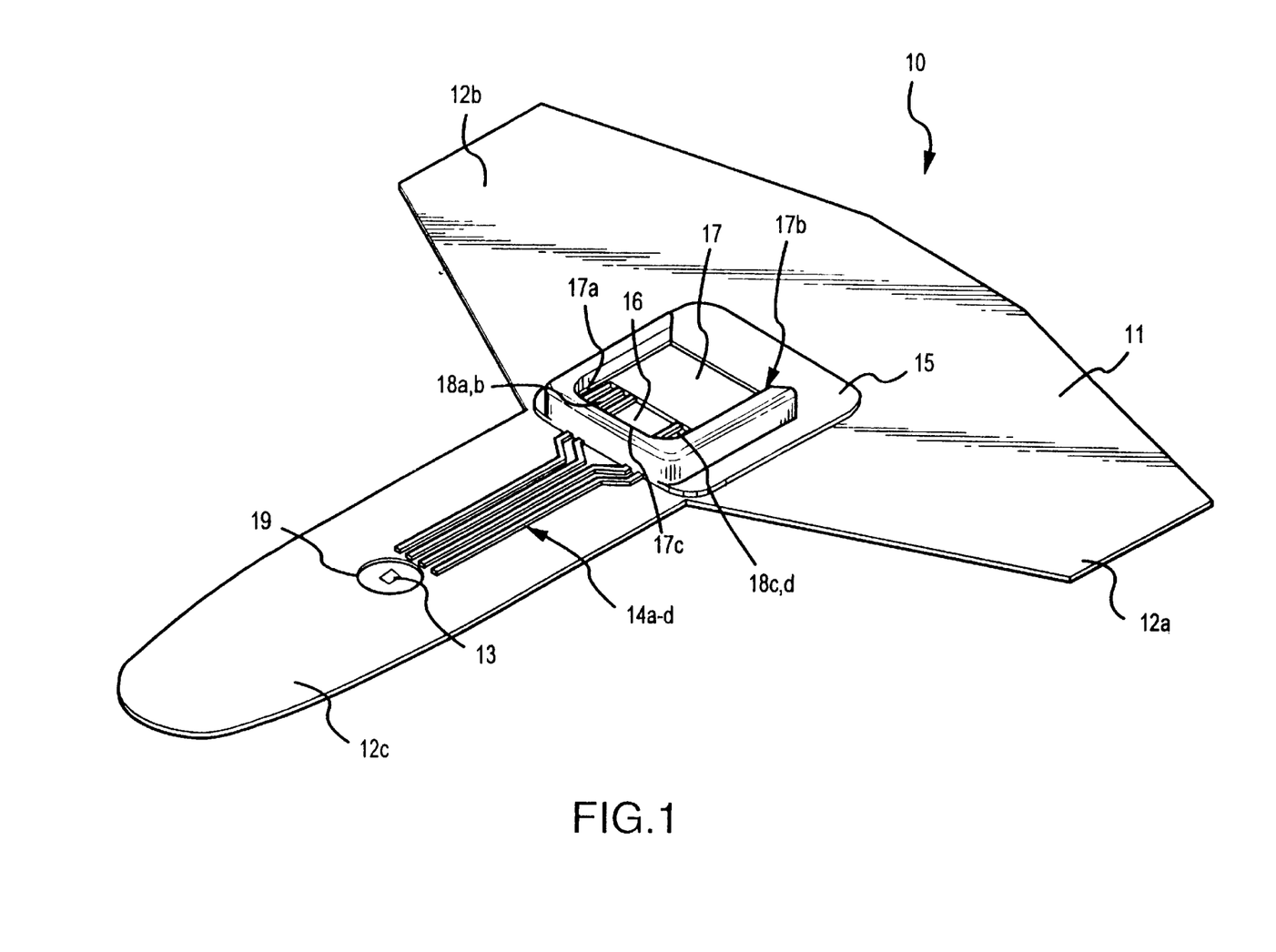
FIG. 1 is a top perspective view of the disposable probe-end of an embodiment of the present invention.
Figure 2:
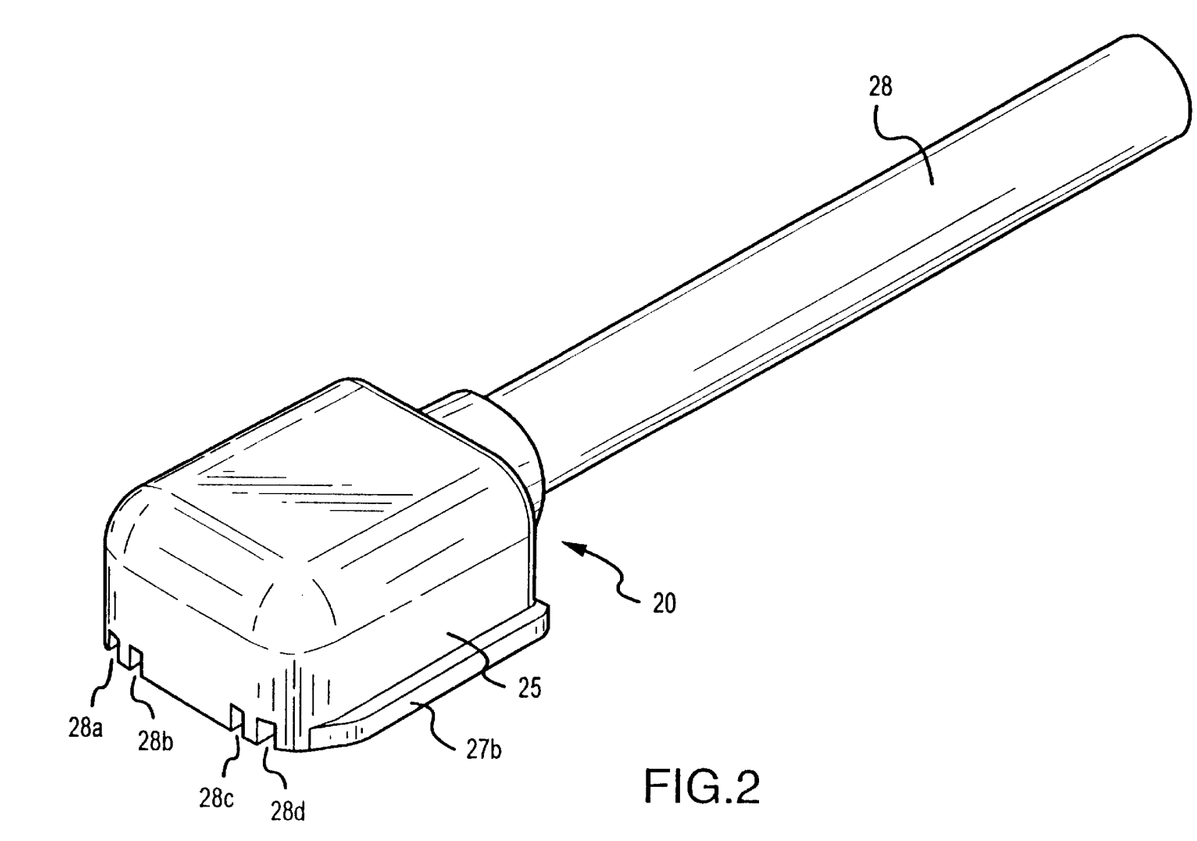
FIG. 2 is top perspective view of the interconnect cable segment of an embodiment of the present invention.

Referring again to FIG. 4 the probe 40 consists of two releasable connected segments: the probe-end 10, separately depicted in FIG. 1 and interconnect cable segment 20, separately depicted in FIGS. 2, 3 and 3b.

Universal probe-end 10 is designed to be disposable and to accommodate any type of interconnect cable segment 20, whether it contains LED's, laser diode, or an optical fiber/mirror for illuminating the tissue. Thus, the construction of probe-end 10 is simple and flexible consisting of a flexible substrate 11 having three portions 12a, 12b and 12c. Substrate portions 12a and 12b are designed to wrap around an appendage of a patient. In FIG. 1 the substrate is designed to be wrapped around a finger. Substrate portions 12a and 12b have an adhesive layer applied to one or more surfaces to enable the portions to be removably attached to the finger. Substrate portions 12a and 12b may be configured differently for attachment of probe-end 10 to the feet of neonates, the smaller fingers of children, or to other appendages of adult, child or neonatal patients.

Substrate portion 12c includes a photodetector 13 which is mounted in an optically transmissive window 19 in the substrate 11 and which is connected to connector 17 through flexible electrical circuits 14 a–d. Connector 17 has three lip portions 17a, 17b, and 17c which are designed to accommodate and hold the connector-end 25 of interconnect cable segment 20. Connector portion 15 provides a larger surface area for connector 17 to be either adhesively affixed to substrate 12 or, alternatively, to be retained between layers of substrate 12. Connector 17 also houses an optically transmissive window 16 and electrical contacts 18a, 18b, 18c, and 18d which connect flexible electrical circuits 14a, b,c and d with interconnect cable segment 20.

Window 16 enables light to be passed from the emitters 21,22,23 and 24 or optical fiber and mirror 29 to the patient while protecting the patient from excess heat and also protecting the reusable interconnect cable segment 20.

FIG. 2 depicts a top elevational view of the patient end of interconnect cable segment 20. Cable 28 consists of a bundle of one or more electrical conductors and, if the emitters are located in the monitor 200, an optical fiber. The electrical conductors and optical fiber are covered by a flexible insulating material to protect the internal components. Conductive grooves 28a, 28b, 28c and 28d provide for electrical interconnection of photodetector 13 through flexible conductors 14a, 14b, 14c and 14d and electrical contacts 18a, 18b, 18c and 18d. Ridge 27b is designed to fit under lip 17b to hold connector-end 25 onto probe-end 10.

FIG. 3 depicts a bottom elevational view of one embodiment of the patient end of interconnect cable segment 20. The embodiments of FIG. 3 includes four emitters 21, 22, 23 and 24. Such an embodiment would be useful in a photoplethysmographic monitor for measuring three or four blood analytes such as oxyhemoglobin, deoxyhemoglobin, carboxyhemoglobin and methemoglobin. Alternatively, the number of emitters could be two in a probe for use with standard pulse oximeters which typically use two emitters having spectral contents characterized by distinct center wavelengths, often 660 nm and 940 nm. Ridges 27a, 27b and 27c fit under lip portions 17a, 17b and 17c to hold connector-end 25 onto probe end 10. The end of latch 30 is designed to click into a hole near the base of lip portion 17c so that upon engagement of the connector-end 25 into connector 17 a releasable latching occurs. In order to disengage the latching mechanism latch 30 is simply depressed.

FIG. 3b depicts essentially the identical interconnect cable segment 25 with the exception that emitters 21, 22, 23 and 24 have been replaced by mirror assembly 29 which reflects light from the optical fiber enclosed in cable 28 which ends near opening 26 through window 16 and onto the tissue of the patient.

While various embodiments of the present invention have been described in detail, it is apparent that modifications and adaptations of those embodiments will occur to those skilled in the art. For example, it should be appreciated that the method and apparatus as taught by the present invention may be modified in an unlimited number of ways within the framework of the teachings of the present invention. These variations are all considered to fall within the scope of the present invention. Therefore, it is to be expressly understood that such modifications and adaptations are within the spirit and scope of the present invention, as set forth in the following claims.

I claim:

1. A probe for illuminating tissue of a subject to measure light absorption of said tissue by a photoplethysmographic measurement system, comprising:

a universal probe-end and an interconnect cable segment having a connector-end;

said universal probe-end comprising:

a flexible substrate for removably affixing said probe-end to said tissue, wherein a first side of the flexible substrate is affixable to contact said tissue;

a connector, fixedly attached to a second side of said substrate, adapted to receive said connector-end of said interconnect cable, wherein said second side of the substrate is opposite to said first side;

a plurality of electrical contacts housed by said connector;

an optically transmissive window housed by said connector;

a photodetector mounted in the flexible substrate; and a first plurality of flexible electrical conductors extending between said photodetector and said plurality of electrical contacts;

said interconnect cable segment comprising a plurality of electrical and/or optically transmissive conductors and a plug at the end opposite said connector-end adapted for electrical and/or optical attachment of said plurality of electrical and/or optically transmissive conductors to one or more specific photoplethysmographic measurement systems, wherein said connector-end further comprises:

a housing having an aperture on one surface, wherein said aperture is aligned with said optically transmissive window upon interconnection of said connector end to said universal probe-end;

a light source located internal to said housing and arranged so as to emit light through said aperture, wherein the optically transmissive window of the universal probe enables the light to pass therethrough to the tissue while protecting the connector-end of the interconnectable cable segment from contamination when the connector end is interconnected to the universal probe-end; and a second plurality of electrical contacts on said connector-end of said interconnect cable adapted to contact said first plurality of contacts, wherein said light source is electrically and/or optically connected to said plurality of electrical and/or optically transmissive conductors, and wherein said second plurality of electrical contacts are electrically connected to said plurality of electrical conductors upon interconnection of said connector end to the universal probe-end.

2. The probe of claim 1 wherein said light source internal said interconnect cable segment housing is a plurality of light emitting diodes and, said plurality of light emitting diodes is electrically connected to said photoplethysmographic measurement system.

3. The probe of claim 1 wherein said light source internal said interconnect cable segment housing is a plurality of laser diodes and, said plurality of laser diodes is electrically connected to said photoplethysmographic measurement system.

4. The probe of claim 1 wherein said light source internal said interconnect cable segment housing is an optical fiber adapted to be illuminated by a plurality of emitters located inside said photoplethysmographic measurement system.

5. The probe of claim 4, further comprising a mirror located internal said housing of said connector-end and adapted to reflect light from said optical fiber through said aperture in said housing.

6. The apparatus of claim 1 wherein said connector of said probe-end comprises:

a u-shaped lip adapted to receive the apertured surface of said connector-end.

7. The apparatus of claim 6, wherein said connector end further comprises a u-shaped ridge adapted to be received under said u-shaped lip of said connector of said probe-end.

8. The apparatus of claim 6, wherein said connector further comprises a latch for releasable latching upon engagement of said connector end into said connector.

9. A probe for illuminating tissue of a subject to measure light absorption of said tissue by a photoplethysmographic measurement system, comprising:

a universal probe-end and an interconnect cable segment having a connector-end;

said universal probe-end comprising:
  a flexible substrate for removably affixing said probe-end to said tissue;
  a connector, fixedly attached to one side of said substrate, adapted to receive said connector-end of said interconnect cable;
  a plurality of electrical contacts housed by said connector;
  an optically transmissive window housed by said connector and said substrate;
  a photodetector Mounted in the flexible substrate; and
  a plurality of flexible electrical conductors extending between said photodetector and said plurality of electrical contacts;

said interconnect cable segment comprising a plurality of electrical and/or optically transmissive conductors, a plug at the end opposite said connector-end adapted for electrical and/or optical attachment of said plurality of electrical and/or optically transmissive conductors to one or more specific photoplethysmorgraphic measurement systems, and means for identifying one or more characteristics of the probe to said photoplethysmographic system, and wherein said connector-end further comprises:

a housing having an aperture on one surface, wherein said aperture is aligned with said optically transmissive window upon the connection of said connector end to said universal probe-end;

a light source located internal to said housing and arranged so as to emit light through said aperture, wherein the optically transmissive window of the universal probe enables the light to pass therethough to tissue of a subject while protecting the connector-end of the interconnectable cable segment from contamination when the connector end is interconnected to the universal probe-end;

a second plurality of electrical contacts on said connector-end of said interconnect cable adapted to contact said first plurality of contacts, wherein said light source is electrically and/or optically connected to said plurality of electrical and/or optically transmissive conductors, and wherein said second plurality of electrical contacts are electrically connected to said pluarality of electrical conductors upon interconnection of said connector end to the universal probe-end.

10. The probe of claim 9, wherein said characteristics of the probe are selected from the group consisting of probe type, photoplethysmographic system manufacturer and actual emitter wavelength.

11. A probe apparatus for illuminating tissue of a subject to measure light absorption of said tissue by a photoplethysmographic measurement system, comprising:

a universal probe end and an interconnect cable segment having a connector-end;

said universal probe-end comprising a photodetector, a connector adapted to receive said connector-end of said interconnect cables and an electrical conductor for connecting said photodetector to said connector, and wherein said probe-end has a opening aperture therein;

said interconnect cable segment including:
  a plurality of emitters for emitting light through said aperture;
  a plurality of electrical conductors connected to said emitters and connectable to said connector;
  a plug at the end opposite said connector-end adapted to electrically connect said plurality of electrical conductors to one of a plurality of photoplethysmographic measurement systems; and
  means for identifying a characteristic of the probe apparatus to said photoplethysmographic system.

12. The probe apparatus of claim 11 wherein the characteristic of the probe apparatus is selected from the group consisting of probe type, photoplethysmographic system manufacturer and actual emitter wavelength.

13. The probe apparatus of claim 12 wherein the identification means comprises one or more electrical elements.

14. The probe apparatus of claim 13 wherein the identification means comprises a plurality of resistors indicative of the actual wavelength of each of the plurality of emitters in said interconnect cable.

15. The apparatus of claim 11, wherein the identified characteristic is employable by the photoplethysmographic system to select a calibration curve for measurement determinations.

16. A probe apparatus for illuminating tissue of a subject to measure light absorption of said tissue by a photoplethysmographic measurement system, comprising:

a universal probe-end and an interconnect cable segment having a connector-end, said universal probe-end comprising a photodetector, a connector adapted to receive said connector-end of said interconnect cable, and an electrical conductor for connecting said photodetector to said connector, wherein said probe-end has an aperture therein;

said interconnect cable segment including:
- a mirror located so as to direct light through said aperture, an optical fiber for directing light from a photoplethysmogmaphic measurement system onto said mirror;
- an electrical conductor connected to said connector;
- a plug at the end opposite said connector-end for optically and electrically connecting said optical fiber and said electrical conductor to one of a plurality of photoplethysmographic measurement systems; and
- a means for identifying a characteristic of the probe apparatus to said photoplethysmographic system.

17. The probe apparatus of claim 16, wherein the characteristic of the probe apparatus is selected from the group consisting of probe type, photoplethysmographic system manufacturer and photodetector type.

18. The probe apparatus of claim 16, wherein the identification means comprises one or more electrical elements.

19. The probe apparatus of claim 18, wherein the identification means comprises a plurality of resistors indicative of the actual wavelength of each of the plurality of emitters in said interconnect cable.

20. The probe apparatus of claim 16, wherein the characteristic of the probe apparatus is selected from the group consisting of probe type, photoplethysmographic system manufacturer and actual emitter wavelength.

21. The probe apparatus of claim 16, wherein the identified characteristic is employable by the photoplethysmogrphic system to select a calibration curve for measurement determinations.

* * * * *

UNITED STATES PATENT AND TRADEMARK OFFICE
CERTIFICATE OF CORRECTION

PATENT NO. : 6,014,576
DATED : January 11, 2000
INVENTOR(S) : Raley

It is certified that error appears in the above-identified patent and that said Letters Patent is hereby corrected as shown below:

At Column 7, Claim 9, line 59, please delete "Mounted" and insert therefor --mounted--.
At Column 8, Claim 9, line 1, please delete "photoplethysmorgraphic" and insert therefor -- photoplethysmographic-- .
At Column 8, Claim 11, line 33, please delete "probe end" and insert therefor -- probe-end -- .
At Column 8, Claim 11, line 37, please delete "cables" and insert therefor -- cable, -- .
At Column 9, Claim 16, line 11, please delete "photoplethysmogmaphic" and insert therefor -- photoplethysmographic-- .
At Column 10, Claim 21, lines 16 and 17, please delete "photoplethysmogrphic" and insert therefor -- photoplethysmographic-- .

Signed and Sealed this

Eighth Day of August, 2000

Attest:

Q. TODD DICKINSON

*Attesting Officer*    *Director of Patents and Trademarks*

UNITED STATES PATENT AND TRADEMARK OFFICE
CERTIFICATE OF CORRECTION

PATENT NO. : 6,014,576
DATED : January 11, 2000
INVENTOR(S) : RALEY

It is certified that error appears in the above-identified patent and that said Letters Patent is hereby corrected as shown below:

At the title page, line [56], please insert
-- 3,943,440 3/1976 Edwards ...... 324/95
4,446,715 5/1984 Bailey ...... 73/1
4,621,643 11/1986 New, Jr. et al. ...... 128/633
4,700,708 10/1987 New, Jr. et al. ...... 128/633
4,770,179 9/1988 New, Jr. et al. ...... 128/633
4,776,339 10/1988 Schreiber ...... 128/633
4,830,014 5/1989 Goodman et al. ...... 128/665
4,867,165 9/1989 Noller et al. ...... 128/633
5,035,243 7/1991 Muz ...... 128/633
5,054,488 10/1991 Muz ...... 128/633
5,090,410 2/1992 Saper et al ....128/633
5,170,786 12/1992 Thomas et al. ...... 128/633
5,209,230 5/1993 Swedlow et al. ...... 128/633
5,339,810 8/1994 Ivers et al. ...... 128/633
5,818,985 10/1998 Merchant et al. ...... 385/20
Re 36,000 12/1998 Swedlow et al. ...... 128/633 --.

Signed and Sealed this

Twentieth Day of February, 2001

Attest:

NICHOLAS P. GODICI

Attesting Officer     Acting Director of the United States Patent and Trademark Office